(12) United States Patent
Tran et al.

(10) Patent No.: US 6,800,648 B2
(45) Date of Patent: Oct. 5, 2004

(54) ANTIPSYCHOTIC AMINOMETHYL DERIVATIVES OF 7,8-DIHYDRO-3H-1,6,9-TRIOXA-3-AZA-CYCLOPENTA[A] NAPHTHALEN-2-ONE

(75) Inventors: Megan Tran, Hoboken, NJ (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/133,994

(22) Filed: Apr. 25, 2002

(65) Prior Publication Data

US 2003/0073697 A1 Apr. 17, 2003

Related U.S. Application Data

(60) Provisional application No. 60/286,565, filed on Apr. 26, 2001.

(51) Int. Cl.[7] .................... C07D 498/04; A61K 31/424; A61P 25/00
(52) U.S. Cl. .................... 514/338; 514/375; 546/271.7; 548/218
(58) Field of Search ................ 514/338, 375; 546/271.7; 548/218

(56) References Cited

U.S. PATENT DOCUMENTS

| | | | |
|---|---|---|---|
| 5,318,988 A | 6/1994 | Schohe-Loop et al. | 514/458 |
| 5,371,094 A | 12/1994 | Heine et al. | 514/323 |
| 5,756,532 A | 5/1998 | Stack et al. | 514/411 |
| 5,869,490 A | 2/1999 | Stack | 514/255 |

FOREIGN PATENT DOCUMENTS

| | | |
|---|---|---|
| EP | WO 97/23485 | 7/1997 |
| WO | WO 91/13872 | 9/1991 |
| WO | WO 97/32871 | 9/1997 |
| WO | WO 98/29415 | 7/1998 |
| WO | WO 98/40386 | 9/1998 |
| WO | WO 00/29397 | 5/2000 |

*Primary Examiner*—Bruck Kifle
(74) *Attorney, Agent, or Firm*—Woodcock Washburn LLP

(57) ABSTRACT

Compounds of the formula

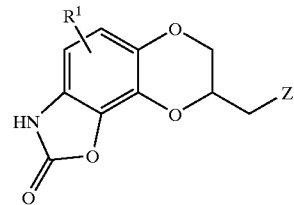

useful for treatment of disorders of the dopaminergic system, such as schizophrenia, schizoaffective disorder, bipolar disorder, Parkinson's disease, L-DOPA induced pychoses and dyskinesias, Tourette's syndrome and hyperprolactinemia and in the treatment of drug addiction such as the addiction to ethanol, nicotine or cocaine and related illnesses.

33 Claims, No Drawings

ANTIPSYCHOTIC AMINOMETHYL DERIVATIVES OF 7,8-DIHYDRO-3H-1,6,9-TRIOXA-3-AZA-CYCLOPENTA[A]NAPHTHALEN-2-ONE

This application claims priority from co-pending provisional application serial No. 60/286,565, filed Apr. 26, 2001, the entire disclosure of which is hereby incorporated by reference.

BACKGROUND OF THE INVENTION

The clinical treatment of schizophrenia has long been defined by the dopamine hypothesis of schizophrenia, which holds that schizophrenia is a result of hyperactivity of dopaminergic neurotransmission, particularly in limbic brain structures such as nucleus accumbens (the mesolimbic dopamine system). Indeed, the positive symptoms of schizophrenia (hallucinations, delusions, thought disorder) are successfully treated with neuroleptics, which block dopamine receptors. However, such treatment is accompanied by the production of movement disorders or dyskinesias (extrapyramidal side effects), due to the blockade of nigrostriatal dopamine receptors. In addition, neuroleptics do not treat the negative symptoms of schizophrenia (social withdrawal, anhedonia, poverty of speech) which are related to a relative hypoactivity of neurotransmission in the mesocortical dopamine system and which respond to treatment by dopamine agonists.

Efforts to induce antipsychotic activity with dopamine autoreceptor agonists have been successful (Corsini et al., Adv. Biochem. Psychopharmacol. 16, 645–648, 1977; Tamminga et al., Psychiatry 398–402, 1986). Dopamine autoreceptor agonists produce a functional antagonism of dopaminergic neurotransmission by the reduction of neuronal firing and the inhibition of dopamine synthesis and release. Since dopamine autoreceptor agonists are partial agonists at postsynaptic dopamine receptors, they provide a residual level of stimulation sufficient to prevent the production of dyskinesias. Indeed, partial agonists are capable of functioning as either agonists or antagonists depending on the level of dopaminergic stimulation in a given tissue or brain region, and would therefore be expected to have efficacy versus both positive and negative symptoms of schizophrenia. Thus, novel dopamine partial agonists are of great interest for the treatment of schizophrenia and related disorders.

DESCRIPTION OF THE INVENTION

In accordance with this invention, there is provided a group of novel antipsychotic agents of the formula:

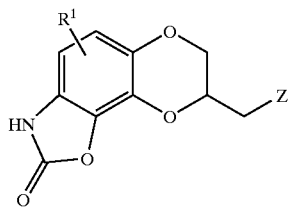

wherein
R$^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Z is defined by N R$^2$—(CH$_2$)$_n$—Y,

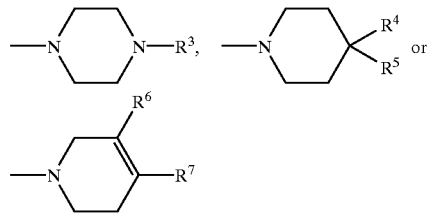

wherein
Y is hydrogen, hydroxy, cycloalkyl of 3 to 15 carbon atoms or phenyl, substituted phenyl, phenoxy, substituted phenoxy, naphthyl, substituted naphthyl, naphthyloxy, substituted naphthyloxy, heteroaryl, substituted heteroaryl, heteroaryloxy or substituted heteroaryloxy, wherein the heteroaryl or the heteroaryl group of heteroaryloxy is selected from thiophene, furan, pyridine, indole, chroman, coumarin, carbostyril, and quinoline;
R$^2$ is hydrogen, benzyl or alkyl of 1 to 6 carbon atoms;
n is an integer from 0 to 6;
R$^3$ is hydrogen, alkyl of 1 to 6 carbon atoms, phenyl, substituted phenyl, ω-phenylalkyl, substituted ω-phenylalkyl, ω-diphenylalkyl, substituted ω-diphenylalkyl, wherein the alkyl chain contains 1 to 4 carbon atoms, indole, substituted indole, indazole, substituted indazole, pyridine, substituted pyridine, pyrimidine, substituted pyrimidine, quinoline, substituted quinoline, benzoisothiazole, substituted benzoisothiazole, benzisoxazole, or substituted benzisoxazole;
R$^4$ is hydrogen, hydroxy, cyano or carboxamido;
R$^5$ is hydrogen, 1-benzimidazol-2-one, benzoisothiazole, or benzisoxazole, each optionally substituted, or —Q—Ar;
Q is C=O, CHOH, or (CH$_2$)$_m$,
m is an integer from 0 to 4;
Ar is phenyl or indole, each optionally substituted; or
R$^4$ and R$^5$, taken together with the carbon atom to which they are attached form

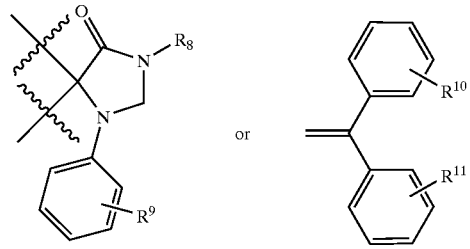

R$^6$ is hydrogen; and
R$^7$ is phenyl, indole, naphthyl, thiophene, benzoisothiazole, or benzisoxazole, each optionally substituted; or
R$^6$ and R$^7$, taken together with the carbon atoms to which they are attached form phenyl or substituted phenyl;
R$^8$ is hydrogen or alkyl of 1 to 6 carbon atoms; and
R$^9$, R$^{10}$ and R$^{11}$ are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof.

In some preferred embodiments of the invention $R^1$ is hydrogen, methoxy or halogen.

In other preferred embodiments of the invention Z is $NR^2$—$(CH_2)_n$—Y.

$R^2$ is, in some aspects of the invention, preferably, hydrogen.

$R^3$ is preferably phenyl, indole, indazole, pyridine, pyrimidine, quinoline, benzoisothiazole, or benzisoxazole each optionally substituted.

In certain preferred embodiments of the invention $R^4$ is hydrogen or hydroxy.

In other preferred embodiments of the invention $R^5$ is 1-benzimidazol-2-one, benzoisothiazole, benzisoxazole, each optionally substituted, or Q—Ar.

Q is preferably C=O or $(CH_2)_m$.

Preferably $R^6$ is hydrogen.

In other preferred embodiments of the invention $R^7$ is phenyl, benzoisothiazole, or benzisoxazole, each optionally substituted.

When taken together, $R^6$ and $R^7$ preferably form phenyl or substituted phenyl.

In some preferred embodiments of the invention $R^1$ is hydrogen, methoxy, or halogen, Z is $NR^2$—$(CH_2)_n$—Y and $R^2$ is hydrogen.

In other preferred embodiments of the invention, Z is

and $R^3$ is phenyl, indole, indazole, pyridine, pyrimidine, quinoline, benzoisothiazole, or benzisoxazole, each optionally substituted. More preferably, $R^1$ is hydrogen, methoxy or halogen, Z is

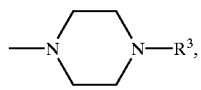

and $R^3$ is phenyl, indole, pyridine, pyrimidine, quinoline, or benzoisothiazole, each optionally substituted.

In still other embodiments of the invention, Z is

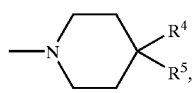

$R^4$ is hydrogen or hydroxy and $R^5$ is 1-benzimidazol-2-one, benzoisothiazole, or benzisoxazole, each optionally substituted. More preferably, $R^1$ is hydrogen, methoxy or halogen, Z is

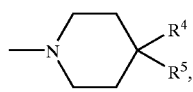

$R^4$ is hydrogen or hydroxy and $R^5$ is 1-benzimidazol-2-one, benzoisothiazole, or benzisoxazole In yet other embodiments of the invention, Z is

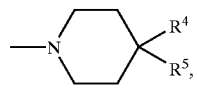

is hydrogen or hydroxy, $R^5$ is —Qr—A, Q is C=O or $(CH_2)_m$, m is 0 to 4, and Ar is phenyl or indole, each optionally substituted. More preferably, $R^1$ is hydrogen, methoxy or halogen, Z is

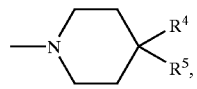

$R^4$ is hydrogen or hydroxy, $R^5$ is —Q—Ar, Q is C=O, and Ar is phenyl or substituted phenyl.

In other preferred embodiments of the invention Z is

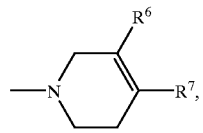

$R^6$ is hydrogen and $R^7$ is phenyl, indole, benzoisothiazole, or benzisoxazole, each optionally substituted. More preferably, $R^1$ is hydrogen, methoxy or halogen, Z is

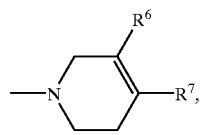

$R^6$ is hydrogen and $R^7$ is phenyl, indole, benzoisothiazole, or benzisoxazole, each optionally substituted.

In still other preferred embodiments of the invention Z is

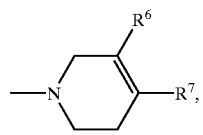

$R^6$ and $R^7$, taken together with the carbon atoms to which they are attached form phenyl or substituted phenyl. More preferably, $R^1$ is hydrogen, methoxy or halogen, Z is

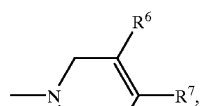

$R^6$ and $R^7$, taken together with the carbon atoms to which they are attached form phenyl or substituted phenyl.

Where a substituent is "substituted" as used herein it may include from 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

This invention relates to both the R and S stereoisomers of the 8-aminomethyl-7,8-dihydro-3H-1,6,9-trioxa-3-aza-cyclopenta[a]naphthalen-2-ones, as well as to mixtures of the R and S stereoisomers. Throughout this application, the name of the product of this invention, where the absolute configuration of the 8-aminomethyl-7,8-dihydro-3H-1,6,9-trioxa-3-aza-cyclopenta[a]naphthalen-2-one is not indicated, is intended to embrace the individual R and S enantiomers as well as mixtures of the two. In some embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Cycloalkyl refers to cyclic alkyl groups including mono-, bi- and polycyclic rings having from 3 to 15 carbon atoms. Representative examples include cyclohexyl and adamantyl.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention include:
8-aminomethyl-7,8-dihydro-3H-1,6,9-trioxa-3-aza-cyclopenta[a]naphthalen-2-one;

8-(benzylamino-methyl)-7,8-dihydro-3H-1,6,9-trioxa-3-aza-cyclopenta[a]-naphthalen-2-one;

8-[(dibenzylamino)-methyl]-7,8-dihydro-3H-1,6,9-trioxa-3-aza-cyclopenta[a]-naphthalen-2-one;

8-[(4-phenyl-butylamino)-methyl]-7,8-dihydro-3H-1,6,9-trioxa-3-aza-cyclo-penta[a]naphthalen-2-one; and 8-[4-(1H-indol-3-yl)-3,6-dihydro-2H-pyridin-1-ylmethyl]-7,8-dihydro-3H-1,6,9-trioxa-3-aza-cyclopenta[a]naphthalen-2-one, or pharmaceutical salts thereof.

The 8-aminomethyl-7,8-dihydro-3H-1,6,9-trioxa-3-aza-cyclopenta[a]-naphthalen-2-ones of the invention in which Z is NR$^2$—(CH$_2$)$_n$—Y are prepared as illustrated below. Specifically, the appropriately substituted nitroguaiacol is alkylated with allyl bromide in the presence of a suitable base such as sodium hydride and then demethylated by a reagent such as sodium hydroxide. The resulting 4-nitro-2-allyloxyphenol is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol is converted to the tosylate by reaction with p-toluenesulfonyl chloride in the presence of a tertiary amine or pyridine or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene and the nitro group reduced to an amine with stannous chloride dihydrate in refluxing ethyl acetate. The amine is then protected with a suitable protecting group such as carbomethoxy or carbobenzoxy via treatment with the appropriate chloroformate and a tertiary base and the olefin is cleaved to the corresponding aldehyde with sodium periodate and catalytic osmium tetroxide. Oxidation of the aldehyde with meta-chloroperoxybenzoic acid (m-CPBA, a Baeyer-Villiger reaction) and cleavage of the resulting formate ester with methanol over basic alumina gives the phenol, which upon treatment with an excess of carbonyl diimidazole (CDI) cyclizes to give the 8-halo- or 8-tosyloxymethyl-7,8-dihydro-3H-1,6,9-trioxa-3-aza-cyclopenta[a]naphthalen-2-one. Replacement of the halide or tosylate group with azide, followed by

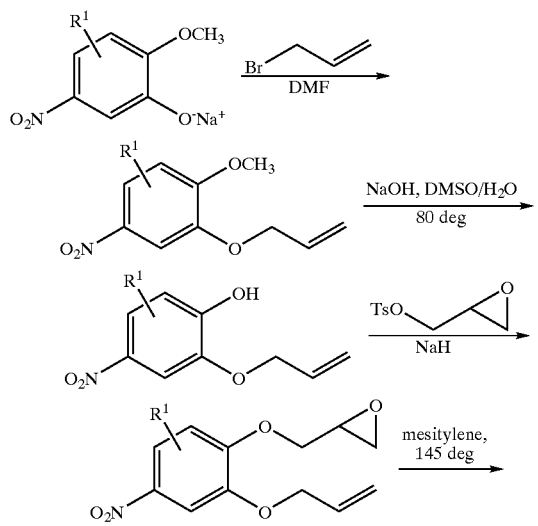

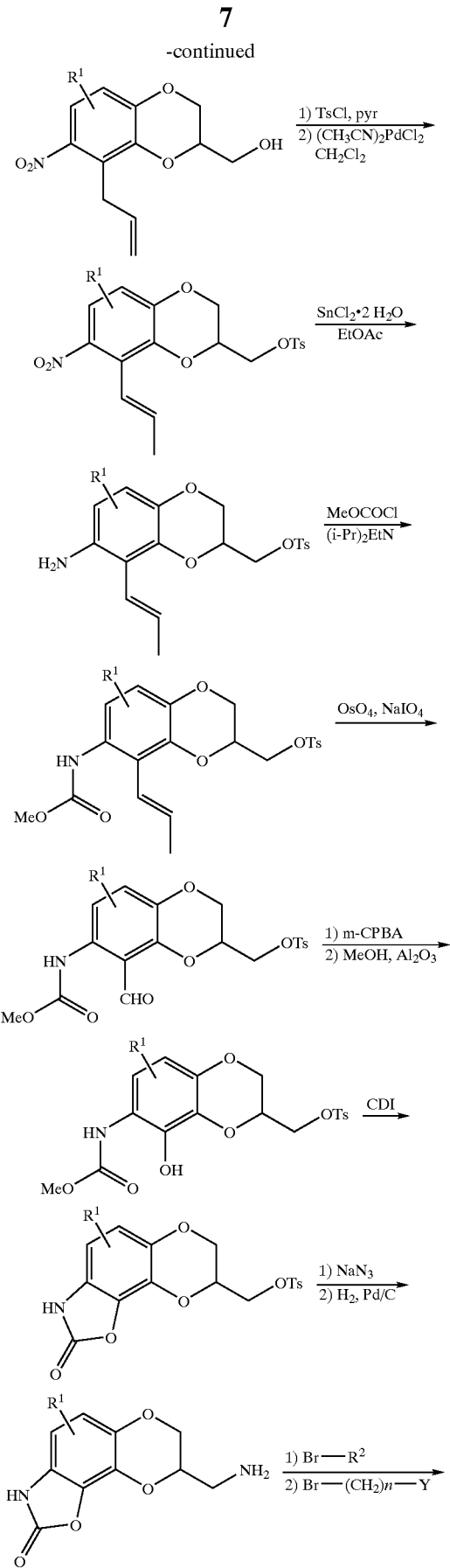

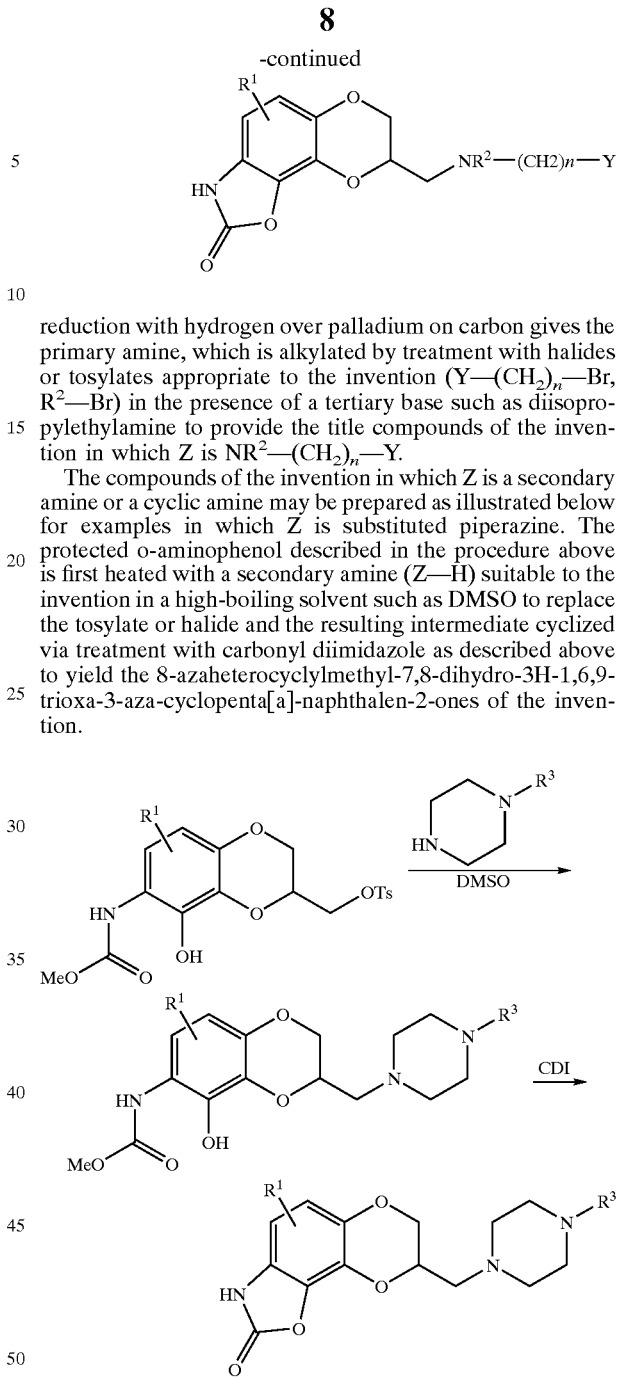

reduction with hydrogen over palladium on carbon gives the primary amine, which is alkylated by treatment with halides or tosylates appropriate to the invention (Y—(CH$_2$)$_n$—Br, R$^2$—Br) in the presence of a tertiary base such as diisopropylethylamine to provide the title compounds of the invention in which Z is NR$^2$—(CH$_2$)$_n$—Y.

The compounds of the invention in which Z is a secondary amine or a cyclic amine may be prepared as illustrated below for examples in which Z is substituted piperazine. The protected o-aminophenol described in the procedure above is first heated with a secondary amine (Z—H) suitable to the invention in a high-boiling solvent such as DMSO to replace the tosylate or halide and the resulting intermediate cyclized via treatment with carbonyl diimidazole as described above to yield the 8-azaheterocyclylmethyl-7,8-dihydro-3H-1,6,9-trioxa-3-aza-cyclopenta[a]-naphthalen-2-ones of the invention.

The guaiacols, catechols and amines appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

The antipsychotic activity of the compounds of the invention was established by a determination of functional antagonism of dopamine receptors in vivo, specifically the compounds' ability to reduce mouse locomotor activity according to the method of Martin and Bendensky, J. Pharmacol. Exp. Therap. 229: 706–711, 1984, in which mice (male, CF-1, Charles River, 20–30 g) were injected with vehicle or various doses of each drug and locomotor activity was measured for 30 minutes using automated infrared activity monitors (Omnitech—8×8 inch open field) located in a darkened room. $ED_{50}$'s were calculated from the horizontal activity counts collected from 10 to 20 minutes after dosing using a nonlinear regression analysis with inverse prediction. When examined in this assay, the compounds of this invention, with the exception of example 3, produce ED50's of less than 50 mg/kg, sc.

Affinity for the dopamine $D_2$ receptor was established by a modification of the standard experimental test procedure of Seemen and Schaus, European Journal of Pharmacology 203: 105–109, 1991, wherein homogenized rat striatal brain tissue is incubated with $^3$H-quinpirole and various concentrations of test compound, filtered and washed and counted in a Betaplate scintillation counter. The results of this testing with compounds representative of this invention are given below.

| Compound | $D_2$ Receptor Affinity ($IC_{50}$ (nM)) |
|---|---|
| Example 1 | 3.7 |
| Example 2 | 0.16 |
| Example 3 | 475 |
| Example 4 | 2.0 |

The compounds of the invention are partial agonists at the $D_2$ sub-family of dopamine receptors. At presynaptic dopamine receptors, the compounds of the invention are autoreceptor agonists; that is, they serve to modulate the synthesis and release of the neurotransmitter dopamine. At postsynaptic dopamine receptors, these compounds are capable of functioning as either agonists or antagonists depending on the level of dopaminergic stimulation. They thus serve to modulate dopaminergic neurotransmission and are thereby useful for treatment of disorders of the dopaminergic system, such as schizophrenia, schizoaffective disorder, bipolar disorder, Parkinson's disease, L-DOPA induced pychoses and dyskinesias, Tourette's syndrome and hyperprolactinemia and in the treatment of drug addiction such as the addiction to ethanol, nicotine or cocaine and related illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 10 mg per day with gradual increase in the daily dose to about 200 mg per day, to provide the desired dosage level in the human.

Provide, as used herein, means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$:hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyloxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$
Calc'd: C, 57.37; H, 5.21; N, 5.58
Found: C, 57.50; H, 5.21; N, 5.43

INTERMEDIATE 4

(8-Allyl-7-nitro-2,3-dihydro-benzo(1,4)dioxin-2-yl)-methanol (R)-2-(2-Allyloxy4-nitrophenoxymethyl)-oxirane (20 g, 80 mmoles) prepared as above was heated at 145–155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$
Calc'd: C, 57.37; H, 5.21; N, 5.58
Found: C, 57.26; H, 5.20; N, 5.35

INTERMEDIATE 5

Toluene-4-sulfonic acid 8-allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$
Calc'd: C, 56.29; H, 4.72; N, 3.45
Found: C, 56.13; H, 4.58; N, 3.44

INTERMEDIATE 6

{17-Nitro-8-[1-propenyl]-2,3-dihydro-1,4-benzodioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$
Calc'd: C, 56.29; H, 4.72; N, 3.45
Found: C, 56.12; H, 4.64; N, 3.39

INTERMEDIATE 7

{7-Amino-8-[1-propenyl]-2,3-dihydro-1,4-benzodioxin-2-yl}methyl 4-methylbenzenesulfonate 10.0 g (24.0 mmole) of {(2R)-7-nitro-8-[1-propenyl]-2,3-dihydro-1,4-benzo-dioxin-2-yl}methyl 4-methylbenzenesulfonate and 28.0 g (123 mmole) of stannous chloride dihydrate were combined and heated to 70° C. in ethyl acetate (250 mL) for 6 hours under nitrogen. After cooling to room temperature, the reaction mixture was poured into ice and was made basic with sodium bicarbonate. It was then extracted with ethyl acetate, washed with brine, dried over magnesium sulfate, filtered and evaporated to a brown oil. The crude oil was then chromatographed on silica gel with 50% hexane/methylene chloride to remove impurities and the desired product Was eluted with 0.5% methanol/$CH_2Cl_2$ to give 8.16 g (91%) of the (R)-enantiomer of the title compound as a yellow oil. For analytical purposes, 50 mg of the yellow oil was crystallized from ethanol with the addition of fumaric acid to give the fumarate of the title compound. MS (ESI) m/z 375 (M+H)+.

Elemental Analysis for: $C_{19}H_{21}NO_5S.1.00\ C_4H_4O_4$
Calc'd: C, 56.20; H, 5.13; N, 2.85
Found: C, 56.40; H, 4.99; N, 2.91

INTERMEDIATE 8

{7-[(Methoxycarbonyl)amino]-8-[1-propenyl]-2,3-dihydro-1,4-benzodioxin-2-yl}methyl 4-methylbenzenesulfonate Methyl chloroformate (2.93 mL, 37.9 mmole) was added to a solution of {(2R)-7-amino-8-[1-propenyl]-2,3-dihydro-1,4-benzodioxin-2-yl}methyl 4-methyl-benzenesulfonate (2.35 g, 6.30 mmole) in ethyl acetate (125 mL), followed by the addition of N,N-diisopropylethylamine (5.50 mL, 31.6 mmole) dropwise over a period of 20 minutes. The solution was stirred under nitrogen at room temperature over a period of 10 hours. This solution was then washed with 2N aqueous HCl, saturated aqueous sodium bicarbonate and brine and dried over magnesium sulfate. Filtration, evaporation in vacuum and column chromatography on silica gel with 0.2% methanol/methylene chloride gave the (R)-enantiomer of the title compound as a white foam (1.90 g, 70%). $^1$H (CDCl$_3$) doublet, 7.8 δ (2 H); doublet, 7.3 δ (3 H); doublet, 6.7 δ (1 H); broad singlet, 6.6 δ (1 H); multiplet, 6.1 δ (2 H); multiplet, 4.4 δ (1 H); multiplet 4.2 δ (3 H); multiplet, 4.0 δ (1 H); singlet, 3.7 δ (3 H); singlet, 2.4 δ (3 H); doublet, 1.9 δ (3 H).

INTERMEDIATE 9

{8-Formyl-7-[(methoxycarbonyl)amino]-2,3-dihydro-1,4-benzodioxin-2-yl}methyl 4-methylbenzenesulfonate To a solution of {(2R)-7-[(methoxycarbonyl)amino]-8-[1-propenyl]-2,3-dihydro-1,4-benzodioxin-2-yl}methyl 4-methylbenzenesulfonate (5.12 g, 11.8 mmole) in tetrahydrofuran (400 mL) was added 2.42 mL of 4% aqueous osmium tetroxide (0.39 mmole). After 0.5 hour, sodium periodate (12.6 g, 59.1 mmole) in water (100 mL) was added dropwise over a period of 1 hour. The heterogeneous solution was stirred under nitrogen at room temperature overnight. The mixture was diluted with water and extracted with ethyl acetate. The organic layer was washed with brine, dried over magnesium sulfate, filtered and concentrated in vacuum to yield the (R)-enantiomer of the title compound as a light beige solid (4.80 g, 97%).

Elemental Analysis for: $C_{19}H_{19}NO_8S.0.2\ H_2O$
Calc'd: C, 53.69; H, 4.60; N, 3.30
Found: C, 53.47; H, 4.45; N, 3.23

INTERMEDIATE 10

{8-Hydroxy-7-[(methoxycarbonyl)amino]-2,3-dihydro-1.4-benzodioxin-2-yl}methyl 4-methylbenzenesulfonate A solution of {(2R)-8-formyl-7-[(methoxycarbonyl)amino]-2,3-dihydro-1,4-benzodioxin-2-yl}methyl 4-methylbenzenesulfonate (8.46 g, 20.0 mmole) in methylene chloride (250 mL) was added dropwise to a solution of 57–86% m-chloro-peroxybenzoic acid (11.5 g, 40–48 mmole) in methylene chloride (120 mL). The reaction was stirred under nitrogen overnight. After dilution to 300 mL with methylene chloride, the solution was washed with saturated sodium aqueous sodium bicarbonate (2×200 mL) and with brine (100 mL), dried over magnesium sulfate, filtered and evaporated to dryness in vacuum. A $H^1$ NMR spectra of the crude product was taken and it was determined to be the intermediate formate ester. Hydrolysis was effected by stirring in methanol over basic alumina for 15 hours. After filtration of the mixture and evaporation of the filtrate in vacuum, the residue was purified by column chromatography on silica gel with 20% hexane/methylene chloride to remove the impurities and methylene chloride to elute the product. Combination of the product fractions and concentration in vacuum gave the (R)-enantiomer of the title compound as a dark green foam (5.41 g, 66%). $^1$H (CDCl$_3$) doublet, 7.8 δ (2 H); doublet, 7.3 δ (2 H); doublet, 7.2 δ (1 H); broad singlet, 6.8 δ (1 H); doublet, 6.4 δ (1 H); broad singlet, 6.0 δ (1 H); multiplet, 4.4 δ(1 H); multiplet, 4.2 δ (3 H); multiplet, 4.0 δ (1 H); singlet, 3.8 δ (3 H); singlet, 2.4 δ (3 H).

INTERMEDIATE 11

[2-Oxo-2,3,7,8-tetrahydro[4,1]dioxino[2,3-g][1,3]benzoxazol-8-yl]methyl 4-methylbenzenesulfonate 1,1'-Carbonyldiimidazole (6.45 g, 39.6 mmole) was added to a solution of {(2R)-8-hydroxy-7-[(methoxycarbonyl)amino]-2,3-dihydro-1,4-benzodioxin-2-yl}-methyl 4-methylbenzenesulfonate (5.40 g, 13.2 mmole) in methylene chloride (400 mL), the solution was refluxed for 4 hours under nitrogen. The solvent was then removed in vacuum and was replaced with 2N aqueous HCl (150 mL). After the mixture had been stirred for 0.5 hour at room temperature, a white solid precipitate, the (R)-enantiomer of the title compound, was removed by filtration, and was dried under high vacuum (5.0 g, >99%).

Elemental Analysis for: $C_{17}H_{15}NO_7S.H_2O$
Calc'd: C, 51.64; H, 4.33; N, 3.54
Found: C, 51.54; H, 4.10; N, 3.47

INTERMEDIATE 12

8-(Azidomethyl)-7,8-dihydro[1,4]dioxino[2,3-g][1,3]benzoxazol-2(3H)-one

Sodium azide (0.86 g, 13.2 mmole) was added to a solution of [(8R)-2-oxo-2,3,7,8-tetrahydro[1,4]dioxino[2,3- g][1,3]benzoxazol-8-yl]methyl 4-methylbenzene-sulfonate (5.0 g, 13 mmole) in dimethylformamide (250 mL). The solution was heated at 70° C. for 9 hours. The solvent was then removed in vacuum and replaced with 300 mL of methylene chloride. The mixture was washed with 300 mL portions of water and saturated brine, dried over magnesium sulfate, filtered and evaporated in vacuum to a yellow solid. The crude solid was column chromatographed on silica gel with 3% methanol in methylene chloride to yield the (S)-enantiomer of the title compound as a white solid (2.86 g, 86%).

Elemental Analysis for: $C_{10}H_8N_4O_4$

Calc'd: C, 48.39; H, 3.25; N, 22.57

Found: C, 48.77; H, 3.25; N, 22.12

EXAMPLE 1

8-Aminomethyl-7,8-dihydro-3H-1,6,9-trioxa-3-aza-cyclopenta[a]naphthalen-2-one (8S)-8-(Azidomethyl)-7,8-dihydro[1,4]dioxino[2,3-g][1,3]benzoxazol-2(3H)-one (2.86 g, 11.5 mmole) in methanol (60 mL) was treated for 24 hours on a Parr shaker with 60 psi of hydrogen in the presence of 0.43 g of 10% Pd/C and 3.0 mL of 4 N isopropanolic HCl. The catalyst was removed by filtration through celite and was washed with additional methanol. The filtrate was evaporated in vacuum to give 2.12 g (68%) of the (S)-enantiomer of the title compound as a beige solid, m.p.>250° C.

Elemental Analysis for: $C_{10}H_{10}N_2O_4$.HCl

Calc'd: C, 46.44; H, 4.29; N, 10.83

Found: C, 46.49; H, 4.11; N, 10.34

EXAMPLE 2

8-(Benzylamino-methyl)-7,8-dihydro-3H-1,6,9-trioxa-3-aza-cyclopenta[a]naphthalen-2-one (8S)-8-Aminomethyl-7,8-dihydro-3H-1,6,9-trioxa-3-aza-cyclopenta[a]-naphthalen-2-one hydrochloride (0.49 g, 1.8 mmole), benzyl bromide (0.20 mL, 1.8 mmole) and 0.31 mL (1.8 mmole) of N,N-diisopropylethylamine were combined in 20 ml DMSO and heated at 50° C. under nitrogen for 6 hours. After completion, the reaction was cooled to room temperature and partitioned between 400 mL each of ethyl acetate and saturated aqueous sodium bicarbonate. The organic phase was removed and washed with brine, dried over magnesium sulfate and concentrated in vacuum. The crude residue was column chromatographed on silica gel using first methylene chloride, then 1% methanol in methylene chloride to elute the dialkylated product and finally 3% methanol in methylene chloride to elute the monoalkylated product (0.16 g, 28%). The latter was recrystallized from ethanol with the addition of a solution of fumaric acid (0.065 g) in hot ethanol to give 0.06 g of the (S)-enantiomer of the title compound as an off-white solid hemifumarate, one-quarter hydrate, m.p. 220° C.

Elemental Analysis for: $C_{17}H_{16}N_2O_4$.0.50 $C_4H_4O_4$.0.25 $H_2O$

Calc'd: C, 60.88; H, 4.98; N, 7.47

Found: C, 61.12; H, 4.73; N, 7.36

EXAMPLE 3

8-[(Dibenzylamino)-methyl]-7,8-dihydro-3H-1,6,9-trioxa-3-aza-cyclopenta[a]naphthalen-2-one Combination of the column chromatography fractions from example 2 which were obtained by elution with 1% methanol in methylene chloride and which contained dialkylated product and concentration of those fractions in vacuum led to the isolation of 0.060 g of the (S)-enantiomer of the title compound as a white crystalline solid, m.p. 210° C.

Elemental Analysis for: $C_{24}H_{22}N_2O_4$.0.50 $H_2O$

Calc'd: C, 70.06; H, 5.63; N, 6.81

Found: C, 70.26; H, 5.33; N, 6.74

EXAMPLE 4

8-[(4-Phenyl-butylamino)-methyl]-7,8-dihydro-3H-1,6,9-trioxa-3-aza-cyclopenta[a]naphthalen-2-one (8S)-8-Aminomethyl-7,8-dihydro-3H-1,6,9-trioxa-3-aza-cyclopenta[a]-naphthalen-2-one hydrochloride (0.40 g, 1.5 mmole), 1-(4-chlorobutyl)benzene (0.24 g, 1.5 mmole), 0.50 mL (2.9 mmole) of N,N-diisopropylethylamine and sodium iodide (0.11 g, 0.73 mmole) were combined in 25 mL DMSO and heated at 70°C. for 6 hours under nitrogen. After completion, the reaction was cooled to room temperature and partitioned between 200 mL each of ethyl acetate and saturated aqueous sodium bicarbonate. The organic phase was washed with brine, dried over magnesium sulfate, filtered and concentrated in vacuum. The crude residue was column chromatographed on silica gel using 5% methanol in methylene chloride to elute the desired product (0.18 g, 52%). The crude free base was crystallized from ethanol with the addition of a solution of fumaric acid (0.06 g) in hot ethanol to give 0.022 g of the (S)-enantiomer of the title compound as a beige solid fumarate, three-quarters hydrate, m.p. 215–218° C.

Elemental Analysis for: $C_{20}H_{22}N_2O_4$.1.00 $C_4H_4O_4$.0.75 $H_2O$

Calc'd: C, 59.56; H, 5.73; N, 5.79

Found: C, 59.50; H, 5.25; N, 5.71

EXAMPLE 5

8-[4-(1H-Indol-3-yl)-3,6-dihydro-2H-pyridin-1-ylmethyl]-7,8-dihydro-3H-1,6,9-trioxa-3-aza-cyclopenta[a]naphthalen-2-one 0.85 g (2.08 mmole) of {(2R)-8-hydroxy-7-[(methoxycarbonyl)amino]-2,3-dihydro-1,4-benzodioxin-2-yl}methyl 4-methylbenzenesulfonate and 1.13 g (5.70 mmole) of 3-(1,2,3,6-tetrahydro-4-pyridinyl)-1H-indole were combined in DMSO (40 mL) and heated at 60° C. under nitrogen for 6 hours. After completion, the reaction was cooled to room temperature and partitioned between 300 mL each of ethyl acetate and saturated aqueous sodium bicarbonate. The organic phase was washed with brine, dried over magnesium sulfate, filtered and concentrated in vacuum to a viscous oil. The crude oil was dissolved in methylene chloride and was heated at reflux in the presence of carbonyl diimidazole (1.02 g) for 4 hours. The reaction was allowed to cool to room temperature and the solvent was removed in vacuum. The residue was column chromatographed on silica gel using first 20% hexane/methylene chloride, then methylene chloride and finally 2% methanol/methylene chloride as eluant. The product fractions were combined and concentrated in vacuum to give 0.080 g of the (S)-enantiomer of the title compound as a light yellow solid, m.p. 202° C.

Elemental Analysis for: $C_{23}H_{21}N_3O_4$.0.50 $H_2O$

Calc'd: C, 66.98; H, 5.38; N, 10.19

Found: C, 66.73; H, 5.33; N, 9.96

What is claimed is:

1. A compound of formula I

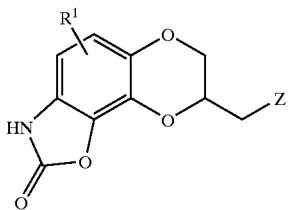

wherein $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Z is defined by $NR^2$—$(CH_2)_n$—Y,

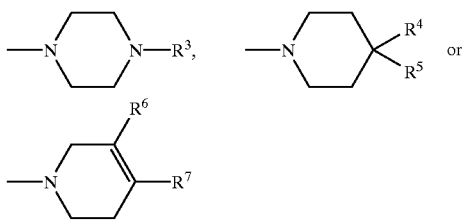

wherein

Y is hydrogen, hydroxy, cycloalkyl of 3 to 15 carbon atoms or phenyl, phenoxy, naphthyl, naphthyloxy, heteroaryl, or heteroaryloxy, wherein the heteroaryl or the heteroaryl group of heteroaryloxy is selected from thienyl, furanyl, pyridinyl indolyl, chromanyl, coumarinyl, carbostyrilyl, and quinolinyl;

$R^2$ is hydrogen, benzyl or alkyl of 1 to 6 carbon atoms;

n is an integer from 0 to 6;

$R^3$ is hydrogen, alkyl of 1 to 6 carbon atoms, phenyl, ω-phenylalkyl, ω-diphenylalkyl, wherein the alkyl chain contains 1 to 4 carbon atoms, indolyl, indazolyl, pyridinyl, pyrimidinyl, quinolinyl, benzoisothiazolyl, or benzisoxazolyl;

$R^4$ is hydrogen, hydroxy, cyano or carboxamido;

$R^5$ is hydrogen, 1-benzimidazol-2-onyl, benzoisothiazolyl, or benzisoxazolyl, or —Q—Ar;

Q is C=O, CHOH, or $(CH_2)_m$, m is an integer from 0 to 4;

Ar is phenyl or indolyl, or $R^4$ and $R^5$, taken together with the carbon atom to which they are attached form

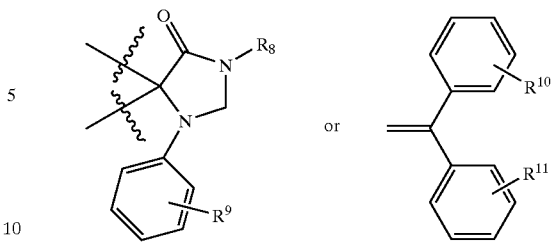

$R^6$ is hydrogen; and $R^7$ is phenyl, indolyl, naphthyl, thienyl, benzoisothiazolyl, or benzisoxazolyl, or $R^6$ and $R^7$, taken together with the carbon atoms to which they are attached form a benzene ring;

$R^8$ is hydrogen or alkyl of 1 to 6 carbon atoms; and $R^9$, $R^{10}$ and $R^{11}$ are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof;

wherein said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

2. A compound of claim 1 wherein $R^1$ is hydrogen, methoxy or halogen.

3. A compound of claim 1 wherein Z is $NR^2$—$(CH_2)_n$—Y.

4. A compound of claim 1 wherein $R^2$ hydrogen.

5. A compound of claim 1 wherein $R^3$ is phenyl, indolyl, indazolyl, pyridinyl, pyrimidinyl, quinolinyl, benzoisothiazolyl, or benzisoxazolyl, each optionally substituted.

6. A compound of claim 1 wherein $R^4$ is hydrogen or hydroxy.

7. A compound of claim 1 wherein $R^5$ is 1-benzimidazol-2-onyl, benzoisothiazolyl, benzisoxazolyl, each optionally substituted or —Q—Ar.

8. A compound of claim 7 wherein Q is C=O or $(CH_2)_m$.

9. A compound of claim 1 wherein $R^6$ is hydrogen.

10. A compound of claim 1 wherein $R^7$ is phenyl, indolyl, benzoisothiazolyl, or benzisoxazolyl each optionally substituted.

11. A compound of claim 1 wherein $R^6$ and $R^7$ taken together form a benzene ring or a substituted benzene ring.

12. A compound of claim 1 wherein $R^1$ is hydrogen, methoxy, or halogen, Z is $NR^2$—$(CH_2)_n$—Y and $R^2$ is hydrogen.

13. A compound of claim 1 wherein Z is

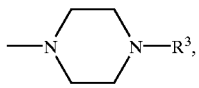

and R³ is phenyl, indolyl, indazolyl, pyridinyl, pyrimidinyl, quinolinyl, benzoisothiazolyl, or benzisoxazolyl, each optionally substituted.

14. A compound of claim 13 wherein R¹ is hydrogen, methoxy or halogen.

15. A compound of claim 13 wherein Z is

R⁴ is hydrogen or hydroxy and R⁵ is 1-benzimidazol-2-onyl, benzoisothiazolyl, or benzisoxazolyl, each optionally substituted.

16. A compound of claim 15 wherein R¹ is hydrogen, methoxy or halogen.

17. A compound of claim 1 wherein Z is

R⁴ is hydrogen or hydroxy, R⁵ is —Q—Ar, Q is C═O or (CH₂)$_m$, m is 0 to 4, and Ar is phenyl or indolyl, each optionally substituted.

18. A compound of claim 17 wherein R¹ is hydrogen, methoxy or halogen, Q is C═O, and Ar is phenyl or substituted phenyl.

19. A compound of claim 1 wherein Z is

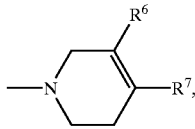

R⁶ is hydrogen and R⁷ is phenyl, indolyl, benzoisothiazolyl, or benzisoxazolyl, each optionally substituted.

20. A compound of claim 19 wherein R¹ is hydrogen, methoxy or halogen.

21. A compound of claim 1 wherein Z is

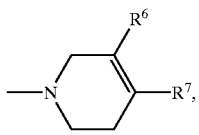

R⁶ and R⁷, taken together with the carbon atoms to which they are attached form a benzene ring or a substituted benzene ring.

22. A compound of claim 21 wherein R¹ is hydrogen, methoxy or halogen.

23. The compound of claim 1 which is 8-aminomethyl-7,8-dihydro-3H-1,6,9-trioxa-3-aza-cyclopenta[a] naphthalen-2-one or a pharmaceutically acceptable salt thereof.

24. The compound of claim 1 which is 8-(benzylamino-methyl)-7,8-dihydro-3H-1,6,9-trioxa-3-aza-cyclopenta[a] naphthalen-2-one or a pharmaceutically acceptable salt thereof.

25. The compound of claim 1 which is 8-[(dibenzylamino)-methyl]-7,8-dihydro-3H-1,6,9-trioxa-3-aza-cyclopenta[a]naphthalen-2-one or a pharmaceutically acceptable salt thereof.

26. The compound of claim 1 which is 8-[(4-phenyl-butylamino)-methyl]-7,8-dihydro-3H-1,6,9-trioxa-3-aza-cyclopenta[a]naphthalen-2-one or a pharmaceutically acceptable salt thereof.

27. The compound of claim 1 which is 8-[4-(1H-indol-3-yl)-3,6-dihydro-2H-pyridin-1-ylmethyl]-7,8-dihydro-3H-1,6,9-trioxa-3-aza-cyclopenta[a]naphthalen-2-one or a pharmaceutically acceptable salt thereof.

28. A method of treating a subject suffering from a condition selected from schizophrenia, schizoaffective disorder, bipolar disorder, Parkinson's disease, L-DOPA induced psychoses or dyskinesias, Tourette's syndrome or hyperprolactinemia which comprises providing to the subject suffering from said condition, a therapeutically effective amount of a compound of formula I

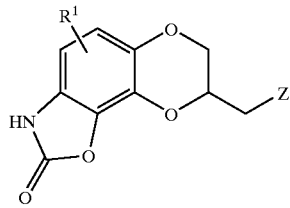

(I)

wherein

R¹ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Z is defined by NR²—(CH₂)$_n$—Y,

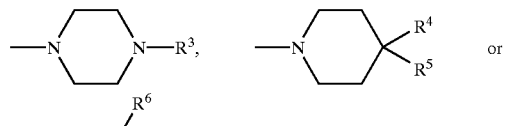 or

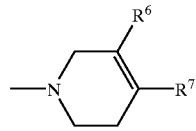

wherein

Y is hydrogen, hydroxy, cycloalkyl of 3 to 15 carbon atoms or phenyl, phenoxy, naphthyl, naphthyloxy, heteroaryl, or heteroaryloxy, wherein the heteroaryl or the heteroaryl group of heteroaryloxy is selected from thienyl, furanyl, pyridinyl, indolyl, chromanyl, coumarinyl, carbostyrilyl, and quinolinyl;

R² is hydrogen, benzyl or alkyl of 1 to 6 carbon atoms;

n is an integer from 0 to 6;

R³ is hydrogen, alkyl of 1 to 6 carbon atoms, phenyl, ω-phenylalkyl, ω-diphenylalkyl, wherein the alkyl chain contains 1 to 4 carbon atoms, indolyl, indazolyl, pyridinyl, pyrimidinyl, quinolinyl, benzoisothiazolyl, or benzisoxazolyl;

R⁴ is hydrogen, hydroxy, cyano or carboxamido;

R⁵ is hydrogen, 1-benzimidazol-2-onyl, benzoisothiazolyl, or benzisoxazolyl, or —Q—Ar;

Q is C=O, CHOH, or (CH$_2$)$_m$,
m is an integer from 0 to 4;
Ar is phenyl or indolyl; or
R$^4$ and R$^5$, taken together with the carbon atom to which they are attached form

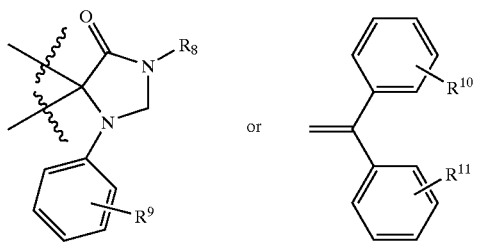

R$^6$ is hydrogen; and
R$^7$ is phenyl, indolyl, naphthyl, thienyl, benzoisothiazolyl, or benzisoxazolyl; or
R$^6$ and R$^7$, taken together with the carbon atoms to which they are attached form a benzene ring;
R$^8$ is hydrogen or alkyl of 1 to 6 carbon atoms; and
R$^9$, R$^{10}$ and R$^{11}$ are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof;
wherein said phenyl, phenoxy, naphthyl, naphthyloxy, heteroaryloxy, ω-phenylalkyl, ω-diphenylalkyl, indoyl, indazolyl, pyridinyl, pyrimidinyl, quinolinyl, benzoisothiazolyl, benzisoxazolyl, 1-benzimidazol-2-onyl, or thienyl groups, or the benzene ring, are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

29. The method of claim 28 wherein the subject is a human.

30. A pharmaceutical composition comprising a compound of formula I

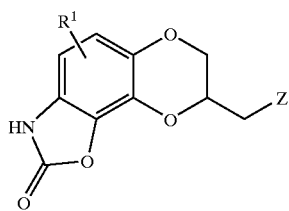

wherein
R$^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Z is defined by NR$^2$—(CH$_2$)$_n$—Y,

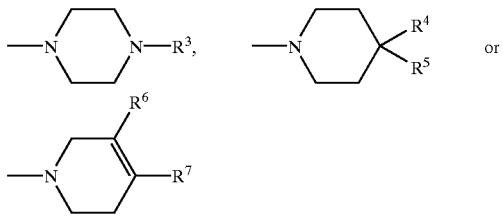

wherein
Y is hydrogen, hydroxy, cycloalkyl of 3 to 15 carbon atoms or phenyl, phenoxy, naphthyl, naphthyloxy, heteroaryl, or heteroaryloxy, wherein the heteroaryl or the heteroaryl group of heteroaryloxy is selected from thienyl, furanyl, pyridinyl, indolyl, chromanyl, coumarinyl, carbostyrilyl, and quinolinyl;
R$^2$ is hydrogen, benzyl or alkyl of 1 to 6 carbon atoms;
n is an integer from 0 to 6;
R$^3$ is hydrogen, alkyl of 1 to 6 carbon atoms, phenyl, ω-phenylalkyl, ω-diphenylalkyl, wherein the alkyl chain contains 1 to 4 carbon atoms, indolyl, indazolyl, pyridinyl, pyrimidinyl, quinolinyl, benzoisothiazolyl, or benzisoxazolyl;
R$^4$ is hydrogen, hydroxy, cyano or carboxamido;
R$^5$ is hydrogen, 1-benzimidazol-2-onyl, benzoisothiazolyl, or benzisoxazolyl, or —Q—Ar;
Q is C=O, CHOH, or (CH$_2$)$_m$,
m is an integer from 0 to 4;
Ar is phenyl or indolyl; or
R$^4$ and R$^5$, taken together with the carbon atom to which they are attached form

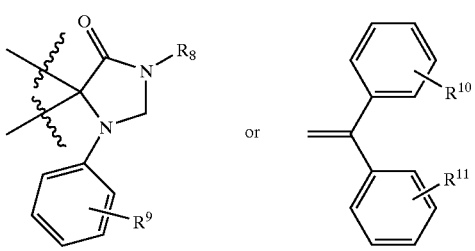

R$^6$ is hydrogen; and
R$^7$ is phenyl, indolyl, naphthyl, thienyl, benzoisothiazolyl, or benzisoxazolyl; or
R$^6$ and R$^7$, taken together with the carbon atoms to which they are attached form a benzene ring;
R$^8$ is hydrogen or alkyl of 1 to 6 carbon atoms; and
R$^9$, R$^{10}$ and R$^{11}$ are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof,
wherein said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2- onyl, or thienyl groups, or the benzene ring, are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

and a pharmaceutically acceptable carrier or excipient.

31. A compound of claim 1 wherein at least one of said phenyl, phenoxy, naphthyl, naphthyloxy, heteroaryloxy, ω-phenylalkyl, ω-diphenylalkyl, indoyl, indazolyl, pyridinyl, pyrimidinyl, quinolinyl, benzoisothiazolyl, benzisoxazolyl, 1-benzimidazol-2-onyl, or thienyl groups, or the benzene ring, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

32. A compound of claim 28 wherein at least one of said phenyl, phenoxy, naphthyl, naphthyloxy, heteroaryloxy, ω-phenyalkyl, ω-diphenylalkyl, indolyl, indazolyl, pyridinyl, pyrimidinyl, quinolinyl, benzoisthiazolyl, benzisoxazolyl, 1-benzimidazol-2-onyl, or thienyl groups, or the benzene ring, bears 1 to 3 substituents selected from hydrogen, halo, cyano, carboxamido, carboalkoxy or two to six carbon atoms, trifluoromethyl, alkyl of 1 to 6 carbon atoms, alkoxy of 1 to 6 carbon atoms, alkanoyloxy of 2 to 6 carbon atoms, alkanamido of 2 to 6 carbon atoms, or alkanesulfonamido of 1 to 6 carbon atoms.

33. A compound of claim 30 wherein at least one of said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

\* \* \* \* \*